(12) United States Patent
Van Den Berg et al.

(10) Patent No.: US 11,098,332 B2
(45) Date of Patent: Aug. 24, 2021

(54) ENZYMATIC REDUCTION OF CYSTINE

(71) Applicant: DSM IP Assets B.V., Heerlen (NL)

(72) Inventors: Marco Alexander Van Den Berg, Echt (NL); Elaheh Jamalzadeh, Echt (NL); Samuel Adrianus Maria Ruinard, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/471,589

(22) PCT Filed: Dec. 14, 2017

(86) PCT No.: PCT/EP2017/082782
§ 371 (c)(1),
(2) Date: Jun. 20, 2019

(87) PCT Pub. No.: WO2018/114575
PCT Pub. Date: Jun. 28, 2018

(65) Prior Publication Data
US 2020/0087688 A1 Mar. 19, 2020

(30) Foreign Application Priority Data

Dec. 22, 2016 (EP) .................................. 16206149

(51) Int. Cl.
*C12P 13/12* (2006.01)
*A23L 27/10* (2016.01)
*A21D 2/24* (2006.01)
*C12P 21/02* (2006.01)

(52) U.S. Cl.
CPC .............. *C12P 13/12* (2013.01); *A21D 2/245* (2013.01); *A23L 27/10* (2016.08); *C12P 21/02* (2013.01)

(58) Field of Classification Search
CPC ...................................................... C12P 13/12
See application file for complete search history.

(56) References Cited

U.S. PATENT DOCUMENTS

| | | | |
|---|---|---|---|
| 5,792,506 A | 8/1998 | Buchanan et al. | |
| 2012/0178128 A1* | 7/2012 | Noordam ................ | C12P 21/02 435/71.1 |
| 2014/0141474 A1 | 5/2014 | Reutter-Maier et al. | |

FOREIGN PATENT DOCUMENTS

| | | |
|---|---|---|
| JP | H03 180188 A | 8/1991 |
| RU | 2 458 981 C2 | 8/2012 |
| WO | 02/061106 A2 | 8/2002 |
| WO | 2011/039156 A1 | 4/2011 |

OTHER PUBLICATIONS

Penninckx, M.J., "An overview on glutathione in *Saccharomyces* versus non-conventional yeasts", FEMS Yeast Research 2 (2002) 295-305.*
Dewey, D.L. & Beecher, J., "Interconversion of Cystine and Cysteine induced by X-rays", Nature, 1965, vol. 206, No. 4991, pp. 1369-1370.*
BRENDA Information for E.C. 1.6.4.2—retrieved Oct. 9, 2020 from < https://www.brenda-enzymes.org/enzyme.php?ecno=1.6.4.2 >.*
PCT International Search Report for PCT/EP2017/082782, dated Mar. 20, 2018.
States, et al., "Thin-Layer Chromatographic Separation of Cystine and the N-Ethylmaleimide Adducts of Cysteine and Glutathione," Analytical Biochemistry, (1969), vol. 27, No. 2: 323-329.
Bulger, et al., "Yeast Glutathione Reductase. I. Spectrophotometric and kinetic studies of its interaction with reduced nicotinamide adenine dinucleotide," The Journal of Biological Chemistry, (1971), vol. 246, No. 18: 5570-5577.

* cited by examiner

*Primary Examiner* — Suzanne M Noakes
(74) *Attorney, Agent, or Firm* — McBee Moore & Vanik IP, LLC (57) ABSTRACT

The present invention relates to a method for the enzymatic reduction of cystine to cysteine comprising contacting cystine with a reduction solution comprising: (i) an active glutathione reductase (EC1.8.1.7); (ii) a cofactor; and (iii) glutathione; and recovering a cysteine comprising composition, wherein the reduction solution has a pH of at least 6 during contacting with cystine.

9 Claims, 5 Drawing Sheets

ENZYMATIC REDUCTION OF CYSTINE

CROSS-REFERENCE TO RELATED APPLICATIONS

This application is the National Stage entry of International Application No. PCT/EP2017/082782, filed 14 Dec. 2017, which claims priority to European Patent Application No. 16206149.3, filed 22 Dec. 2016.

BACKGROUND

Field

The present invention relates to a method for the enzymatic reduction of cystine to cysteine. According to another aspect, the present invention relates to a composition comprising cysteine and to the use thereof as natural food flavour. According to yet another aspect, the present invention relates to a reduction solution and the use thereof.

Description of Related Art

Cysteine, mainly the L-enantiomer, is a precursor in the food, pharmaceutical and personal care industries. One of the larger food applications is the production of flavours. For example, the reaction of cysteine with sugars in a Maillard reaction yields meat flavours. Cysteine is also used as a processing aid for baking and is added to natural fruit juice products as antioxidant. When used as a food additive, cysteine has the E number E920. As pharmaceutical it is applied to improve hepatic function and pigmentation. In clinical nutrition cysteine is added to amino acid infusions as an antioxidant agent. In the field of personal care, cysteine is used for permanent wave applications (predominantly in Asia), wherein cysteine is used for breaking up the disulfide bonds in the hair's keratin.

Cysteine and L-cysteine are referring to the same molecule and both terms can be used interchangeably. Similarly, cystine and L-cystine can be used interchangeably. Cysteine, abbreviated as Cys or C, is a semi-essential amino acid, meaning it can be synthesized by human from methionine, but in some cases such as for infants, elderly and disease it needs to be obtained from the diet such as broccoli, garlic, onion and meat. The cysteine thiol group not only plays an important role in structural stabilization but more importantly as the reactive part of the molecule. The thiol side chain often participates in enzymatic reactions, acting as a nucleophile like in proteases and acyltransferases. The thiol is susceptible to oxidization to give the disulfide bridges, which serves an important structural role in many proteins. Other possible post-translational modifications are sulphenation (SOH), sulphination ($SO_2H$), nitrosylation (SNO), glutathionylation, which acts as a regulatory switch responsive to the cellular redox state.

Cysteine has been traditionally obtained from animal hair via chemical hydrolysis. However, serious problems exist, such as avoidance of animal hair use for safety, low productivity and concerns about environmental pollution. Therefore, there has been a strong demand for environmentally friendly methods for production of cysteine. More recently methods to produce cysteine comprise fermentation using recombinant microorganisms. One known method is the use of recombinant *E. coli* producing >20 gram of cysteine per liter. However, a problem is that in solution oxidization of cysteine readily leads to the disulfide cystine, which needs to be reduced.

Conventional methods for production of cysteine are electrochemical methods using electrochemical reduction of cystine. A drawback of using electrolysis is that the provided cysteine cannot be classified as natural as intended in the European regulation on Flavourings, because electrolysis is a physical process which intentionally modifies the chemical nature of the cysteine.

WO2011/039156 discloses a process for producing cysteine employing yeast. The examples show a non enzymatic reduction of cystine because the glutathione reductase enzymes of the yeast are inactive at 51° C. and at a pH of 5.9 as is shown in examples 4 and 5 below. In addition, by the use of cream yeast the amount of glutathione added to the reaction is sufficient to drive the reduction of cystine towards cysteine. A drawback of the method disclosed in WO2011/039156 is that the process requires a long time and the cysteine yield is low.

Given the above, there is a need in the art for a method for the reduction of cystine to cysteine for which the obtained cysteine can be classified as natural.

SUMMARY

The present invention relates to a method for the enzymatic reduction of cystine to cysteine. According to another aspect, the present invention relates to a composition comprising cysteine and to the use thereof as natural food flavour. According to yet another aspect, the present invention relates to a reduction solution and the use thereof.

DETAILED DESCRIPTION OF A PREFERRED EMBODIMENT

An object of the invention is therefore to provide a method in which the reduction is conducted at improved conditions. Another object of the invention is to provide a method involving reduction which requires a reduced amount of energy. A further object of the invention is to provide a method wherein the dosage of starting material such as enzyme and/or mediator may be reduced and at the same time output of the reduced cysteine is maintained at the same level or even increased. A still further object of the present invention is to provide a method involving reduction wherein the reduction from cystine to cysteine is complete. Yet another object is to provide a method for the reduction of cystine wherein the formed cysteine is qualified as natural flavoring ingredient.

The above objects, amongst other objects, are solved by the present invention. Specifically, the above objects, amongst other objects, are solved by providing a method for the enzymatic reduction of cystine to cysteine comprising contacting cystine with a reduction solution comprising:
  (i) an active glutathione reductase (EC1.8.1.7);
  (ii) a cofactor; and
  (iii) glutathione;
  and recovering a cysteine comprising composition,
  wherein the reduction solution has a pH of at least 6 during contacting with cystine.

Surprisingly, the inventors of the present invention found that a complete reduction of cystine to cysteine can be obtained by using the method of the present invention. It is found that where non enzymatic reduction of cystine generally results in an equilibrium between oxidized cystine and reduced cysteine, or complete reduction if the reducing agent is added in excess, the present enzymatic reduction enables the reaction towards 100% cysteine without adding mediator and/or cofactor in excess. Accordingly, in a preferred embodiment the present invention is a method for the enzymatic reduction of cystine to cysteine wherein 100% of the cystine is reduced. Advantageously, the cysteine recovered in the present method qualifies as a natural cysteine because enzymatic processes with microorganisms such as bacteria and yeasts or isolated enzymes are permitted for the production of natural flavouring ingredients.

Enzymatic reduction, as used in the present context, is intended to mean that the cystine is reduced towards cysteine by contacting the cystine with glutathione in the presence of an active glutathione reductase (EC1.8.1.7), wherein the active glutathione reductase (EC1.8.1.7) reduces the glutathione after oxidation of the glutathione.

Active glutathione reductase (EC1.8.1.7), as used in the present context, means that the enzyme is active in its function to reduce glutathione. Preferably, the glutathione reductase remains active during the step of contacting the cystine with the reduction solution. More preferably the glutathione reductase remains active during the entire step of contacting the cystine with the reduction solution.

A cofactor, as used in the present context, is intended to mean a helper molecule that assists the thiol reducing enzyme. Preferably the cofactor is a coenzyme. Suitable examples of cofactor are reduced nicotinamide adenine dinucleotide (also abbreviated as NADH) or reduced nicotinamide adenine dinucleotidephosphate (also abbreviated as NADPH), or flavin adenine dinucleotide (also abbreviated as $FADH_2$).

Recovering the cysteine, as used in the present context, means recovering the cysteine from the reduction solution. The cysteine may be recovered from the reduction solution by techniques known in the art. Suitable examples of techniques which can be used for the recovery of the cysteine may comprise the use of membranes, crystallization, chromatography and combinations thereof.

In a preferred embodiment, the present step of recovering the cysteine comprising composition is carried out within 15 hours after the step of contacting cystine with the reduction solution. More preferably the present step of recovering the cysteine comprising composition is carried out within 12 hours, more preferably within 9 hours, most preferably within 6 or even 3 hours, after the step of contacting cystine with the reduction solution. More preferably, the present step of recovering the cysteine comprising composition is carried out after 0.5 hour after the step of contacting cystine with the reduction solution.

The present cystine may be provided by known methods in the art for the production of cystine. For example the present cystine may be provided by fermentation and biocatalysis. The fermentation may be carried out using recombinant microorganism. Biocatalysis may be carried out by using enzymes from recombinant microorganisms. The present cystine may also be provided as a mixture of cystine and cysteine in a pure or diluted form.

In a preferred embodiment, the present glutathione is added to the present reduction solution in a composition comprising more than 1% (wt), preferably more than 2% (wt) glutathione on dry weight of the composition, such as more than preferably 5%, 10%, 20% or even 50%. More preferably the present glutathione is in purified or in isolated form, i.e. in a composition comprising more than 90% (wt) glutathione or more than 95% (wt) glutathione. It is advantageous to use glutathione which is in purified form since this simplifies the downstream processing to recover the cysteine. A mediator in purified form, or alternatively in isolated form, means that the glutathione is present and/or is added to the present reduction solution as an individual agent, for example without being present as compound in a microorganism or cell free extract.

The present glutathione might be in oxidized form (also abbreviated as GSSG) or in reduced form (also abbreviated as GSH). Glutathione is a suitable mediator for the glutathione reductase. The inventors of the present invention found that the separate addition of glutathione to a reduction solution comprising glutathione reductase results in an increased or even complete reduction of cystine towards cysteine. Further, the present inventors found that enzymatic reduction of GSSG is an efficient method to provide GSH, and contributes to a complete reduction of cystine. Further, enzymatic reduction of GSSG provides an improved method by reducing the production costs because GSH is expensive.

The molar ratio of the glutathione:cystine in the reduction solution is preferably less than 1. Preferably the molar ratio of glutathione:cystine is less than 0.7, 0.6, 0.5, 0.4, 0.3, 0.2, 0.1, 0.05 or less than 0.01. More preferably the molar ratio of glutathione: cystine is between 0.01 and 0.7, such as between 0.02 and 0.6. Preferably the present molar ratio of glutathione to cystine is the molar ratio of glutathione to cystine present in the reduction solution. The ratio of glutathione to cystine can be calculated by dividing the molar amount of glutathione which is present in the reduction solution by the molar amount of cystine which is present in the reduction solution. The present inventors found that the addition of glutathione to the reduction solution results in an increased reduction of cystine to cysteine. It is surprising that low amounts of glutathione, such as lower amounts of glutathione than cystine, result in a high reduction of cystine to cysteine. It is advantageous to use less amounts of glutathione since this simplifies the downstream processing for providing the cysteine.

In a preferred embodiment, the present glutathione reductase is added in purified or in isolated form. It is advantageous to use a glutathione reductase which is in purified form since this simplifies the downstream processing to recover the cysteine. Alternatively, the glutathione reductase enzyme is immobilized on a support.

In another preferred embodiment the present glutathione reductase is comprised in a microorganism. In a more preferred embodiment the present glutathione reductase is comprised in a permeabilized microorganism. More preferably the present glutathione reductase is comprised in a cell free extract derived from a microorganism. A cell free extract comprises the soluble molecules of a cell obtained after breaking open the cells. Preferably the present cell free extract does not comprise cell walls. Preferably the present cell free extract is derived from fungi such as *Penicillium, Trichoderma, Aspergillus* or yeast. More preferably the cell free extract is derived from *Penicillium* or yeast strains belonging to the genera *Saccharomyces, Kluyveromyces* or *Candida*. Most preferably the cell free extract is derived from *Saccharomyces cerevisiae*. Examples of genera of suitable bacterial microorganisms are Clostridia, *Escherichia*, and Archaea such as *Methanobacterium* and *Methanosarcina*. The use of cell free extracts is advantageous since existing large scale production capacity of for example bakers' yeast or fungal or bacterial fermentations for enzyme production can be efficiently used for the provision of cell free extracts. Furthermore, the use of cell free extracts to provide the glutathione reductase eliminates the need to use purified glutathione reductase which come at an expense. Another advantage of using cell free extracts is that the cell free extracts may contain amounts of glutathione and/or thioredoxin (or other similar molecules) which function as (natural) mediator in the present reduction solution.

The use of the cell free extract's endogenous mediator provides a cost and material efficient method for the reduction of cystine.

More preferably the cell free extract is derived from yeast by enzymatic, mechanical, chemical or physical disruption of yeast cells followed by separating the soluble fraction from the cells walls to provide the cell free extract. A cell free extract is preferably obtained by homogenization techniques. Homogenization techniques may include mixing or milling with particles such as sand and/or glass beads. It was found advantageous to use cell free extracts derived from yeast because the reduction may benefit from the entire yeast cell redox system. In a preferred embodiment, the permeabilized cells are derived from cells by methods known in the art, such as, but not limited to, freezing-and-thawing cycles, autolysis, DMSO treatment, ethanol or toluene treatment. Preferably, the cell free extract is obtained without a heating step. More preferably the cell free extract is obtained without a heating step with a temperature which inactivates the glutathione reductase. Examples of temperatures which inactivate the glutathione reductase are above 40° C., above 45° C., above 50° C. or even above 55° C.

In a preferred embodiment, the present reduction solution further comprises (iv) a cofactor regeneration system. The use of a cofactor regeneration system provides an improved process for the enzymatic reduction of cystine since no extra step is necessary for addition of cofactor during the course of the reduction. Furthermore, it is cost efficient to regenerate cofactor since lower amounts of cofactor are needed to provide the reduction of cystine to cysteine. Preferably the cofactor regeneration system comprises an enzyme and a corresponding substrate. Preferably the cofactor regeneration system comprises glucose dehydrogenase and glucose and/or formate dehydrogenase and formate. Formate dehydrogenase is found particularly suitable for the regeneration of NADH, whereas glucose dehydrogenase is suitable for regeneration of both NADPH and NADH. Alternative enzymes in the present cofactor regeneration system are alcohol dehydrogenase, an NADP-dependent formate dehydrogenase, glucose 6-phosphate dehydrogenase, $H_2$-driven $NAD(P)^+$-reducing hydrogenase or phosphite dehydrogenase. Particularly preferred is a cofactor regeneration system comprising alcohol dehydrogenase and an alcohol, more preferably alcohol dehydrogenase with isopropanol or alcohol dehydrogenase with ethanol. The advantage of using alcohol dehydrogenase with an alcohol as substrate is that the products formed by the alcohol dehydrogenase, such as acetone after using isopropanol and acetaldehyde after using ethanol, are volatile and therefore they could be easily removed from the present reduction solution and/or cysteine comprising solution.

In a preferred embodiment, the temperature of the present reduction solution is within the range of 2° C. to 90° C., preferably during contacting the cystine with the reduction solution. Preferably the temperature is within the range of 10° C. to 60° C. More preferably the temperature of the reduction solution is within the range of 15° C. to 50° C. Most preferably the temperature of the reduction solution is within the range of 15° C. to 40° C. ° C., such as 20° C., 21° C., 22° C., 23° C., 24° C., 25° C., 26° C., 27° C., 28° C., 29° C., 30° C., 31° C., 32° C., 33° C., 34° C., 35° C. 36° C., 37° C., 38° C. or 39° C.

In a preferred embodiment, the pH of the present reduction solution has a pH within the range of pH 6 to 10, preferably during contacting the cystine with the reduction solution. Preferably the pH is within the range of 6.5 to 9. More preferably the pH of the reduction solution is within the range of 6.5 to 8.5 or 7.0 to 8.5, such as pH 7.1, 7.2, 7.3, 7.4, 7.5, 7.6, 7.7, 7.8, 7.9, 8.0, 8.1, 8.2, 8.3 and 8.4. The inventors of the present invention found that using a pH within the range of 6 to 8.5 an increased reduction of cystine is obtained. Surprising is that at a pH within the range of 7 to 8.5 an even higher or even complete reduction of cystine is obtained.

In yet a further preferred embodiment of the present invention, the present cofactor added to the present reduction solution is in oxidized form, such as nicotinamide adenine dinucleotide phosphate (NADP+) or oxidized nicotinamide adenine dinucleotide (NAD+). The present inventors found that in the present method the reduction of cystine can be obtained by using cofactor in oxidized form. The use of cofactor in oxidized form provides an improved method because the cofactor in oxidized form is readily available and thus cost efficient. If a cofactor regeneration system is present in the present reduction solution, the use of cofactor in oxidized form avoids an additional step in advance to reduce the cofactor. since the cofactor in oxidized form will be reduced by the cofactor regeneration system. If a flavin adenine dinucleotide ($FADH_2$)-dependent enzyme system is used, oxidized flavin adenine dinucleotide (FAD+) could be added to the present reduction solution.

In a preferred embodiment of the present method, the present cystine is contacted with the reduction solution for a time period which is sufficient to reduce more than 50%, preferably more than 60%, more preferably more than 70%, even more preferably more than 80%, most preferably more than 90% or 99% or even 100% of the cystine to cysteine. Preferably the time period is less than 48 hours, more preferably less than 24 hours, even more preferably less than 12 hours, most preferably less than 6 or less than 3 hours. More preferred is a time period from 1 to 3 or 1.5 to 2.5 hours. The inventors found that the present method is a time efficient method for the reduction of cystine, even when the method is carried out on industrial scale. Thus, the present invention provides improved conditions for the reduction of cystine.

In a preferred embodiment, contacting the cystine with the reduction solution is carried out under low aerobic or even more preferred under anaerobic conditions to reduce or to prevent reoxidation of cysteine to cystine. Therefore, the advantage of using anaerobic conditions is the increased amount of cysteine in the present reduction solution.

In a preferred embodiment, the method of the invention is carried out on industrial scale. Throughout the description of the invention, an industrial scale method or an industrial process may be understood to encompass a method using a reduction solution having a volume scale which is $\geq 10$ L, preferably $\geq 100$ L, more preferably $\geq 1$ m$^3$, $\geq 5$ m$^3$, even more preferably $\geq 10$ m$^3$, most preferably $\geq 25$ m$^3$, preferably less than 250 m$^3$.

In another preferred embodiment, the present reduction contains low, i.e. less than 5% (wt) or less than 1% (wt) or no compounds that can catalyze the reoxidation of cysteine to cystine. Examples of such compounds that have a tendency to 'adsorp' electrons, are ferric iron, nitrate, cupric ions. The advantage is an increased amount of cysteine in the present reduction solution.

In yet another preferred embodiment the present reduction solution is an aqueous solution. Preferably the reduction solution or aqueous solution comprises a buffer. Preferably the buffer is a sodium phosphate buffer. Alternatively, the buffer is a tris(hydroxymethyl)aminomethane buffer (or tris HCl buffer) or a 2-(N-morpholino)ethanesulfonic acid buffer (abbreviated as MES buffer).

In a preferred embodiment, the present cysteine comprising composition recovered in the present method comprises cysteine and one or more compounds which was present in the reduction solution during contacting the cystine with the reduction solution. Preferably, the present cysteine comprising composition recovered in the present method comprises cysteine and one or more selected from gluconic acid, gluconate, formic acid, glucose, formate, nicotinamide adenine dinucleotide phosphate, nicotinamide adenine dinucleotide, glutathione, acetone, acetaldehyde and glutathione reductase. The present reduction solution comprises several ingredients such as glutathione, cofactor and thiol reducing enzyme. The present recovery of the cysteine comprising composition may comprise one or more of the ingredients present in the reduction solution.

Given that the present method provides cysteine which can beneficially be qualified as natural, the present invention relates, according to another aspect, to a composition comprising cysteine, or L-cysteine, and one or more selected from gluconic acid, gluconate, formic acid, glucose, formate, nicotinamide adenine dinucleotide phosphate, nicotinamide adenine dinucleotide, glutathione (GSH or GSSG) and a glutathione reductase. Preferably the present composition is obtainable by the present method for the enzymatic reduction of cystine to cysteine. More preferably the present composition is obtained by the present method.

Preferably, the present composition or the present cysteine comprising composition recovered in the present method comprises cysteine and/or at least 1 ppm, at least 10 ppm or at least 100 ppm of one or more selected from gluconic acid, gluconate, formic acid, glucose, formate, nicotinamide adenine dinucleotide phosphate, nicotinamide adenine dinucleotide, glutathione acetone, acetaldehyde, glutathione (GSH or GSSG) and a glutathione reductase.

Preferably, the present composition or the present cysteine comprising composition recovered in the present method comprises cysteine and/or at least 1 ppb, at least 10 ppb or at least 100 ppb of one or more selected from gluconic acid, gluconate, formic acid, glucose, formate, nicotinamide adenine dinucleotide phosphate, nicotinamide adenine dinucleotide, glutathione, acetone, acetaldehyde, glutathione (GSH or GSSG) and glutathione reductase.

More preferably, the present composition or the present cysteine comprising composition recovered in the present method comprises cysteine, and at most 1 ppm, at most 10 ppm or at most 100 ppm of one or more selected from gluconic acid, gluconate, formic acid, glucose, formate, nicotinamide adenine dinucleotide phosphate, nicotinamide adenine dinucleotide, glutathione, acetone, acetaldehyde, glutathione (GSH or GSSG) and a glutathione reductase.

More preferably, the present composition or the present cysteine comprising composition recovered in the present method comprises cysteine, and at most 1 ppb, at most 10 ppb or at most 100 ppb of one or more selected from gluconic acid, gluconate, formic acid, glucose, formate, nicotinamide adenine dinucleotide phosphate, nicotinamide adenine dinucleotide, glutathione, acetone, acetaldehyde, glutathione (GSH or GSSG) and a glutathione reductase.

Most preferably, the present composition or the present cysteine comprising composition recovered in the present method comprises cysteine and gluconic acid, cysteine and formic acid, or cysteine, and glutathione (GSH or GSSG).

The advantage of the present composition is that it comprises substantially cysteine which is obtained by the present enzymatic reduction of cysteine, and thus is considered as natural cysteine. Therefore, the present composition can advantageously be used as a natural food flavour or as a natural ingredient for the production of food or for the production of food flavours.

MATERIALS AND METHODS

1. Materials

The following materials where used in the examples.
L-Cystine, Sigma-aldrich, C7602-25G
Glutathione Reductase from baker's yeast (*S. cerevisiae*), Sigma-aldrich, G3664-2.5KU
L-Glutathione reduced, Sigma-aldrich, G4251-100G
L-Glutathione oxidized, Sigma-aldrich, G4376-10G
Thioredoxin Reductase from *Escherichia coli*, Sigma-aldrich, T7915-250UG
Thioredoxin from *Escherichia coli*, Sigma-aldrich, T-0910-1 MG
B-Nicotinamide adenine dinucleotide phosphate, reduced tetra (cyclohexylammonium) salt, Sigma-aldrich, N5130-25MG
B-Nicotinamide adenine dinucleotide reduced disodium salt hydrate, Sigma-aldrich, N8129-50MG
B-Nicotinamide adenine dinucleotide phosphate hydrate, Sigma-aldrich, N5755-110MG
B-Nicotinamide adenine dinucleotide hydrate, Sigma-aldrich, N1636-100MG
Glucose dehydrogenase from *Pseudomonas* sp., Sigma-aldrich, 19359-10MG-F
Formate dehydrogenase from *Candida boidinii*, Sigma-aldrich, F8649-50UN
D(+)-Glucose, Anhydrous, Merck, CAS 50-99-7, Calbiochem
Sodium formate, Sigma-aldrich, 71539-500G
di-sodium hydrogen phosphate dihydrate, Merck, CAS No 10028-24-7
sodium dihydrogen phosphate monohydrate, Merck, CAS No 10049-21-5

2. Reaction

The reactions of the present examples are carried out in a reduction solution which is a sodium phosphate buffer. First a saturated L-cystine solution was made by stirring >500 mg/L L-cystine in sodium phosphate buffer (pH 6.0 or pH 8.0) for 1 hour at room temperature. Further the additional optional ingredients such as thiol reducing enzyme, mediator, cofactor and cofactor regeneration system were added. The reaction was carried out at room temperature (20-25° C.) for 2 hours. The reaction was stopped by adding a deuterium oxide solution comprising 40 g/l malic acid, 100 mg/l 1.1-difluoro-1-trimethylsilanyl methylphosphonic acid (FSP), having a pH of 6.4 with 50% NaOH and incubation for 1 hour.

3. NMR Analysis

The obtained reduction solution comprising L-cysteine was analysed by NMR for L-cystine and free thiol groups. Samples were measured in 3 mm NMR tubes on a 700 MHz spectrometer equipped with a helium-cooled cryoprobe. NOESYGPPR1d.COMP water suppression was applied. 32 Scans were acquired with a relaxation delay of 1.2 seconds. Components were quantified according to the integrals of the peaks relative to the peak area of FSP at 0 ppm:

D 5.04 ppm: glucose
Dd 3.18 ppm: Cystine
Dd 3.09 ppm: GSSG
M 2.24 ppm: total SH.

4. % Cystine Reduction

The percentage (%) reduction of cystine was calculated by subtracting the amount of cystine at the end of the reaction from the amount of cystine at the start of the reaction, and dividing this number by the amount of cystine at the start of the reaction, multiplied with 100.

EXAMPLES

Example 1

Ratio's Mediator: L-Cystine

175 µl L-cystine solution (pH 8.0) was pipetted to a 96-well plate. Five µl of the following were added to a final reaction volume of 200 µl: glutathione reductase (17 U/ml); NADH or NADPH (1.0 and 0.28 mM); glucose dehydrogenase (3.4 U/ml) and D-glucose (2 mM); if applicable Milli-Q™ water. Finally five µl of different glutathione concentrations were added (see FIGS. 1 and 2) to a final reaction volume of 200 µl. The final L-cystine concentration in the reaction was 0.85 mM final reaction. Reactions were executed as described in the materials and methods and the L-cystine and free thiol groups were analyzed by NMR.

Figure 1:
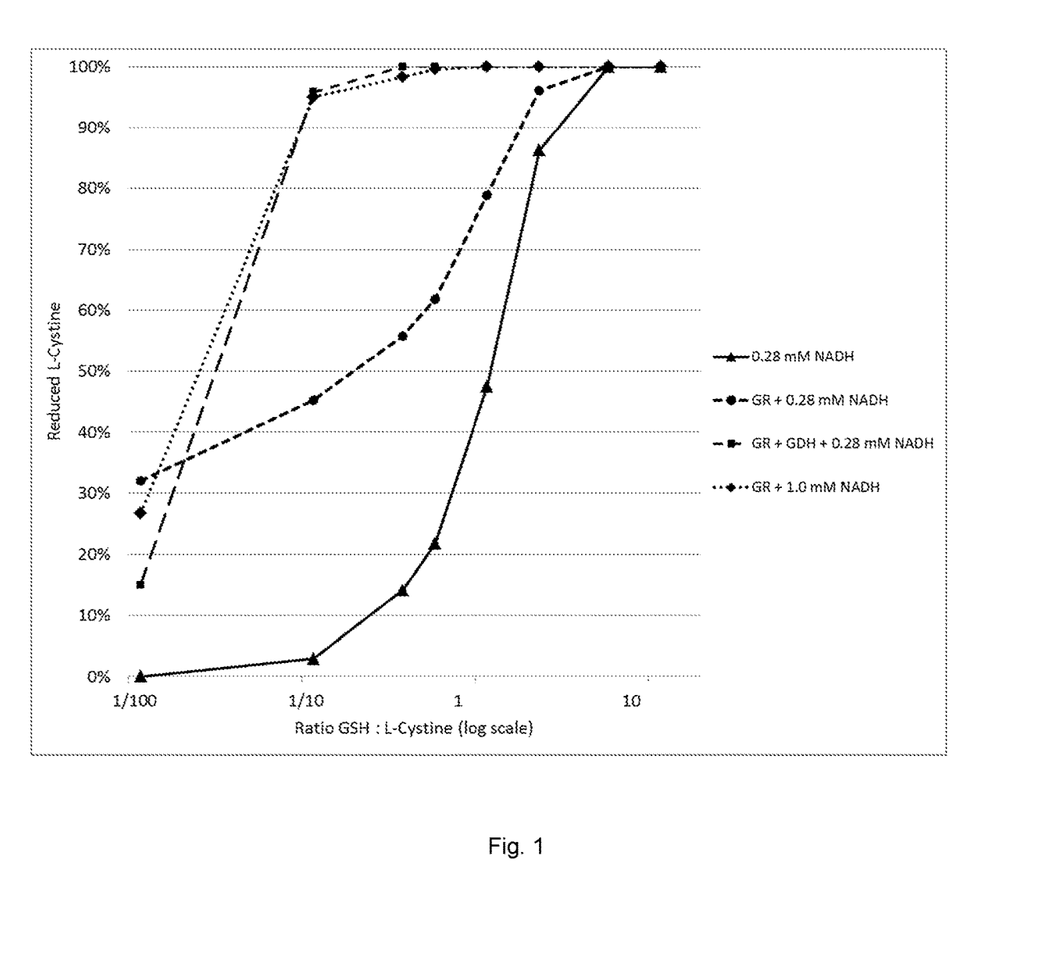
FIG. 1: Percentage reduced L-Cystine in several reaction setups with varying glutathione concentrations and NADH as cofactor.

FIG. 1 shows the percentage of reduced L-cysteine with varying glutathione concentrations. Specifically, FIG. 1 shows that the non-enzymatic reduction in the first series with only GSH and NADH provides a reduction above 90% only if much more GSH than L-cystine is present. Surprisingly, after addition of glutathione reductase, an increased reduction is obtained at lower ratio's of GSH:L-cystine.

Further, FIG. 1 shows that with the presence of a cofactor regeneration system like glucose dehydrogenase and D-glucose even lower amounts of mediator are needed to provide a reduction above 90%, surprisingly enabling a significant reduction of the ratio of GSH:L-cystine. Moreover, the added cofactor regeneration system is able to reduce cystine at a reduction above 90% at much lower cofactor NADH concentrations (since 0.28 mM NADH results in the same reduction towards L-cysteine as with an excess amount of 1.0 mM NADH) as compared to without a cofactor regeneration system.

Figure 2:
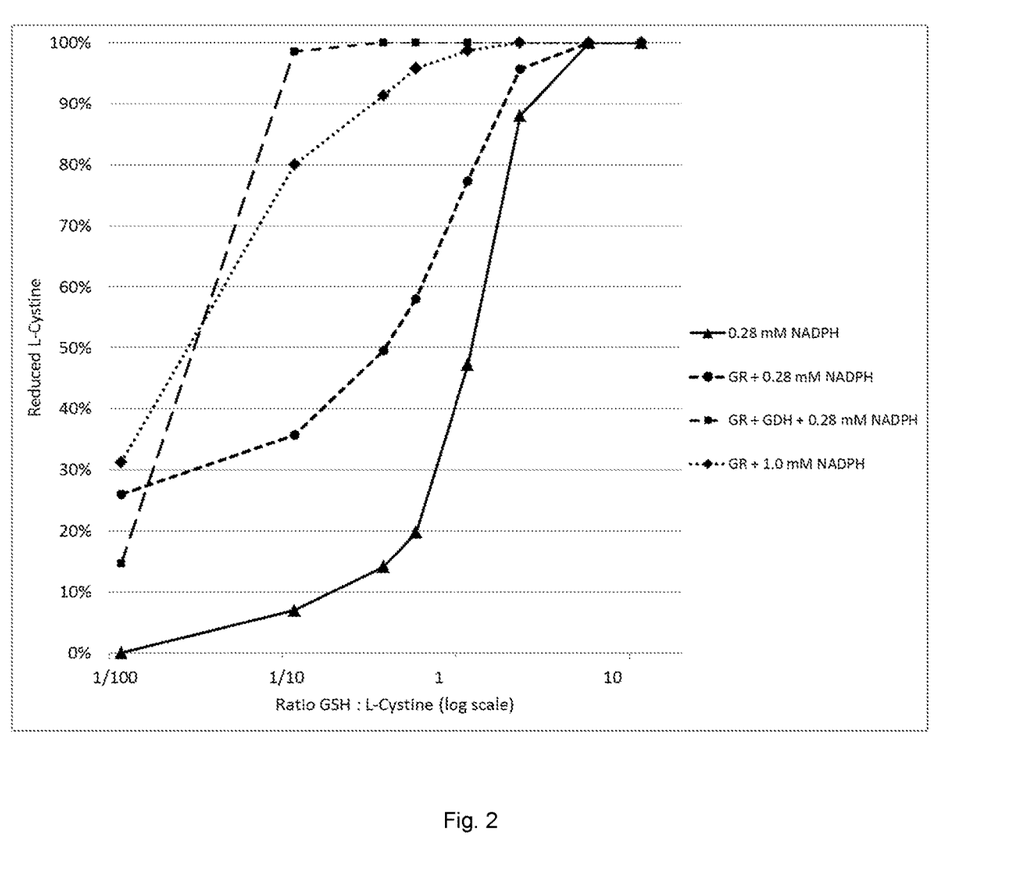
FIG. 2: Percentage reduced L-Cystine in several reaction setups with varying glutathione concentrations and NADPH as cofactor.

Analogous to FIG. 1, FIG. 2 discloses that a reduction of L-cystine towards L-cysteine of higher than 90% can be obtained with NADPH as cofactor, even if the ratio of glutathione: L-cystine is less than 1. Here, the addition of a cofactor regeneration system is able to reduce cystine at a reduction above 90% not only at much lower cofactor NADPH concentrations (since 0.28 mM NADPH results in the same reduction towards L-cysteine as with an excess amount of 1.0 mM NADPH) as compared to without a cofactor regeneration system, it also surprisingly allows for an even further reduction of the ratio of GSH:L-cystine.

To conclude, FIG. 1 and FIG. 2 disclose the feasibility of the present invention in providing an improved method for the reduction of L-Cystine.

Example 2

Reduction Using Cell Free Extract (Abbreviated as CFE)

CFE Preparation

Yeast (*Saccharomyces cerevisiae*) and fungal (*Penicillium chrysogenum*) cell cultures were washed with Milli-Q™ water, suspended in 100 mM Tris-HCL buffer (pH 7.5) and stored on ice. Cells were transferred to 2.0 ml vials containing 0.5 g of 0.45-0.5 mm glass beads and thoroughly shaken three-times at 5000 rpm for 40 seconds on a Precellys homogenizer with cooling on ice in between. Extract was centrifuged twice, while transferring supernatant to fresh tubes after each centrifugation step. Total protein content of cell free extract (CFE) was determined according to the Biuret Method. Samples were stored at −20° C. until further use.

Assay:

185 µl L-Cystine solution (pH 6.0 or 8.0) was pipetted to a 96-well plate. Five µl of the following were added to a final reaction volume of 200 µl: yeast (1 mg/ml) or fungal (0.5 mg/ml) CFE; mediator L-glutathione (100 µg/ml); NADH (700 µg/ml) or NADPH (800 µg/ml); if applicable Milli-Q™ water. L-cystine concentrations were 0.63 mM at pH6.0 and 0.78 mM at pH 8.0 in the final reaction. Reactions (see Table 2) were executed as described in the materials and methods and the L-cystine and free thiol groups were analyzed by NMR.

TABLE 2

Overview of L-Cystine reduction reactions using CFE and percentage reduction

| Substrate | pH | CFE | mediator | co-factor | Reduction |
|---|---|---|---|---|---|
| L-cystine | 6 | *S. cerevisiae* | — | NADH | 0 |
| | | | GSH | | 32 |
| | | | — | NADPH | 1 |
| | | | GSH | | 33 |
| | | *Penicillium* chr. | — | NADH | 0 |
| | | | GSH | | 30 |
| | | | — | NADPH | 0 |
| | | | GSH | | 37 |
| | 8 | *S. cerevisiae* | — | NADH | 6 |
| | | | GSH | | 31 |
| | | | — | NADPH | 0 |
| | | | GSH | | 100 |
| | | *Penicillium* chr. | — | NADH | 7 |
| | | | GSH | | 47 |
| | | | — | NADPH | 2 |
| | | | GSH | | 72 |

Table 2 clearly shows that at pH 8 the reduction of L-cystine is increased. Further, it is clear from Table 2 that CFE's of *S. cerevisiae* and *Penicillium* chr. are able to provide the reduction of L-cystine.

Example 3

Co-Factor Regeneration

175 µl L-cystine (pH 8.0) was pipetted to a 96-well plate. Five µl of the following were added to a final reaction volume of 200 μl: glutathione reductase (17 U/ml) or yeast CFE (1 mg/ml); mediator L-glutathione (100 μg/ml); NADH or NADPH (200 and 350 μg/ml); glucose dehydrogenase (GDH) or formate dehydrogenase (FDH) (both 3.4 U/ml); D-glucose or sodium formate (both 1 mM); if applicable Milli-Q™ water. L-cystine concentrations were 0.80 mM and 0.52 mM in purified enzyme and CFE reactions respectively. Reactions (see Table 3) were executed as described in the materials and methods and the L-cystine and free thiol groups were analyzed by NMR.

TABLE 3

Reaction setup for co-factor regeneration with purified enzyme or CFE and percentage of reduced L-Cystine.

| Substrate | Mediator | Co-factor | Reducing enzyme | Regenerating enzyme | Regenerating substrate | Reduction % |
|---|---|---|---|---|---|---|
| L-cystine | GSH | NADH | — | GDH | glucose | 10 |
| | | | glutathione reductase | — | — | 14 |
| | | | | GDH | glucose | 91 |
| | | | | FDH | formate | 100 |
| | | NADPH | — | GDH | glucose | 15 |
| | | | glutathione reductase | — | — | 30 |
| | | | | GDH | glucose | 100 |
| | | | | FDH | formate | 100 |
| | | NADH | Yeast CFE | — | — | 9 |
| | | | | | glucose | 0 |
| | | | | | formate | 6 |
| | | | | GDH | glucose | 28 |
| | | | | FDH | formate | 100 |
| | | NADPH | | — | — | 55 |
| | | | | | glucose | 68 |
| | | | | | formate | 68 |
| | | | | GDH | glucose | 100 |
| | | | | FDH | formate | 79 |

Table 3 clearly shows that by using a cofactor regeneration system the reduction of cystine is obtained, while only limited amounts of cofactor NADH or NADPH are used (200 and 350 μg/ml, whereas in example 1 and 3 700 and 800 μg/ml are used, respectively). Further, Table 3 shows that by using cell free extract in combination with cofactor regeneration 100% reduction of cystine is obtained.

Example 4

Oxidized Cofactor
175 μl L-cystine solution (pH 8.0) was pipetted to a 96-well plate. Five μl of the following were added to a final reaction volume of 200 μl: glutathione reductase (17 U/ml); mediator L-glutathione (1 mM); NADH, NAD+, NADPH or NADP+ (all 1 mM); glucose dehydrogenase (3.4 U/ml) and D-glucose (2 mM); if applicable Milli-Q™ water. L-cystine concentration was 0.96 mM in final reactions. Reactions (see Table 4) were executed as described in the materials and methods and the L-cystine and free thiol groups were analyzed by NMR.

Table 4 shows that using a cofactor in oxidized form results in a 100% reduction of cystine.

Example 5 pH Dependent Activity of Yeast Glutathione Reductase

Figure 3:
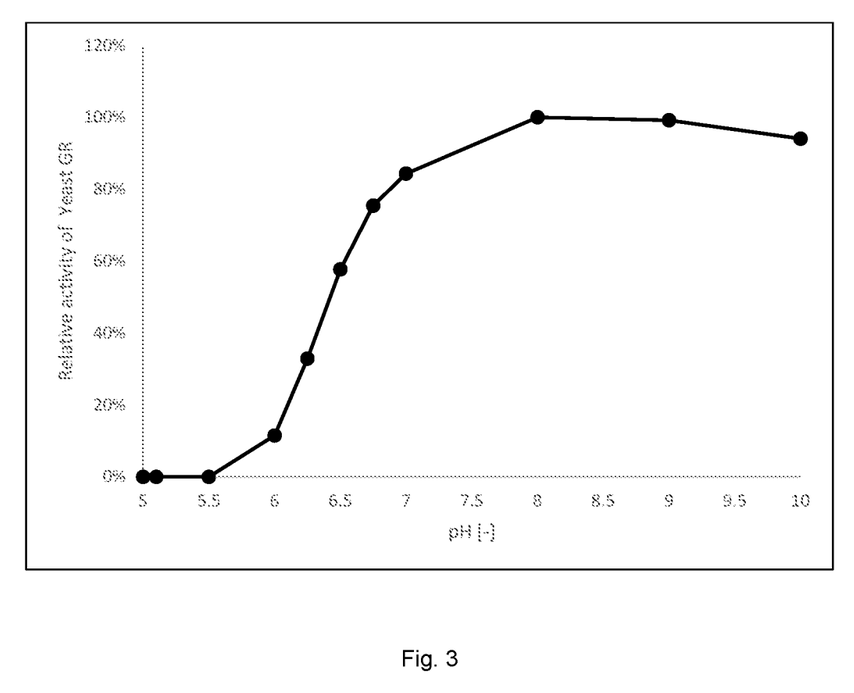
FIG. 3: pH activity curves for yeast Glutathione reductase. Activities are corrected for the background conversion of NADPH at the different acidities and expressed relative to the highest activity observed between pH 5 and 10.

The pH curve for yeast Glutathione Reductase (GR) enzyme was obtained by assaying the activity at every pH unit between pH 5 and 10 in 0.1 M phosphate buffer. A blank without GR enzyme was included at every pH. The buffers for pH 5-9 were mix buffers of 0.1 M Na2HPO4 solution and 0.1M NaH2PO4 solution. Addition of sodium hydroxide was required for reaching a buffer pH 10. An NADPH stock of 50 mM was prepared in milliQ water with added sodium hydroxide to pH 8, where NADPH is soluble and stable. The GSSG solutions were prepared separately for each pH (20 mM=61.3 mg/5 mL buffer in 15 mL Greiner tube). The enzyme was first diluted 20× in water and then 100× in buffer at the different pH set points. The NADPH stock solution was diluted 25× in the desired buffer briefly before starting the assay to minimize the background conversion of NADPH before addition of enzyme. The assay was performed as follows: 100 microliter GSSG solution pH X+50 microliter NADPH solution pH X+50 microliter diluted enzyme pH X. Subsequently, a kinetic readout with decrease in absorption at 340 nm per minute at desired pH was carried out. The slopes of the reactions (Δ340 nm/min) were corrected for the slope of the blank reaction at the same pH and

TABLE 4

Reactions with reduced-and oxidized co-factor and percentage of reduced L-Cystine.

| Substrate | Reducing enzyme | Mediator | Co-factor | Regenerating enzyme | Regenerating substrate | Reduction (%) |
|---|---|---|---|---|---|---|
| L-Cystine | Glutathione Reductase | GSH | NADH | Glucose Dehydrogenase | D-Glucose | 100 |
| | | | NAD+ | | | 100 |
| | | | NADP+ | | | 100 |
| | | | NADPH | | | 100 | activities were expressed relative to the highest measured activity for the enzyme. The relative activity is shown in FIG. 3.

Example 6

Cystine Reduction in Presence of Enzyme at Different Process Conditions.

Figure 4:
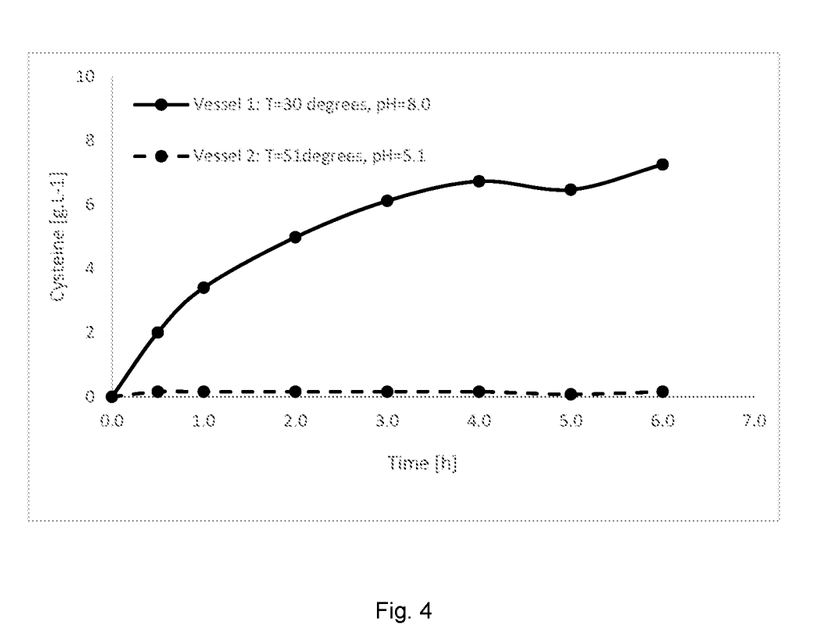
FIG. 4: formation of cysteine in time using yeast GR under different process conditions

Reduction of cystine to cysteine was carried out in presence of oxidized glutathione as mediator and NADP+ as cofactor using yeast glutathione reductase (sigma) and Glucose dehydrogenase in order to regenerate NAPPH in the reaction. The schematic reaction is as follows:

CYS-CYS+2GSH→2CYS+GSSG  Reaction 1:

GSSG+NADPH→2GSH+NADP+H  Reaction 2:

Glucose+NADP→Gluconic acid+NADPH  Reaction 3:

The enzymatic conversion was performed in a 200 ml jacketed vessel with temperature and pH control. The total working volume was 100 ml. Reactions were performed in two vessels. Both vessels contained yeast GR (Sigma) and Glucose dehydrogenase (GDH 105, Codexis). Reactions were performed two different process conditioned indicated in Table 5 below.

TABLE 5

Amounts of components and process conditions applied in reduction of Cystine using yeast GR and GDH enzymes (in 100 mL)

| compounds | Vessel 1 | Vessel 2 |
| --- | --- | --- |
| Yeast GR (Sigma) | 2 units/ml | 2 units/ml |
| GDH 105 (Codexis) | 2 units/ml | 2 units/ml |
| GSH (g) | 0.12 | 0.12 |
| Cystine (g) | 1.0 | 1.0 |
| NADPH (g) | 0.0076 | 0.0076 |
| Temperature (° C.) | 30 | 51 |
| pH | 8.0 | 5.1 |

Samples were taken at t=0 (before addition of enzyme), 0.5, 1, 2, 3, 4, 5, and 6 hours. 200 µl sample was centrifuged 1 minute at 13.000 RPM and 100 µl supernatant was transferred to 900 µl 0.111N HCL (final concentration of 0.1N HCL), mixed and stored at −20° C. All samples were analyzed by LCMS-MS Method to measure L-cystine, L-cysteine, GSH, GSSG and combinations of these components. The cysteine formation in time is illustrated in FIG. 4.

The Level of cysteine in vessel 2, did not increase in time showing that the yeast glutathione reductase was not active under applied conditions of 51° C. and pH 5.1. The initial increase of cysteine in this reaction is the result of non enzymatic reduction with GSH and does not further increase as glutathione reductase is not active and thus cannot reduce the oxidized glutathione.

Example 7

Stability of Glutathione Reductase at 55° C. Temperature

Figure 5:
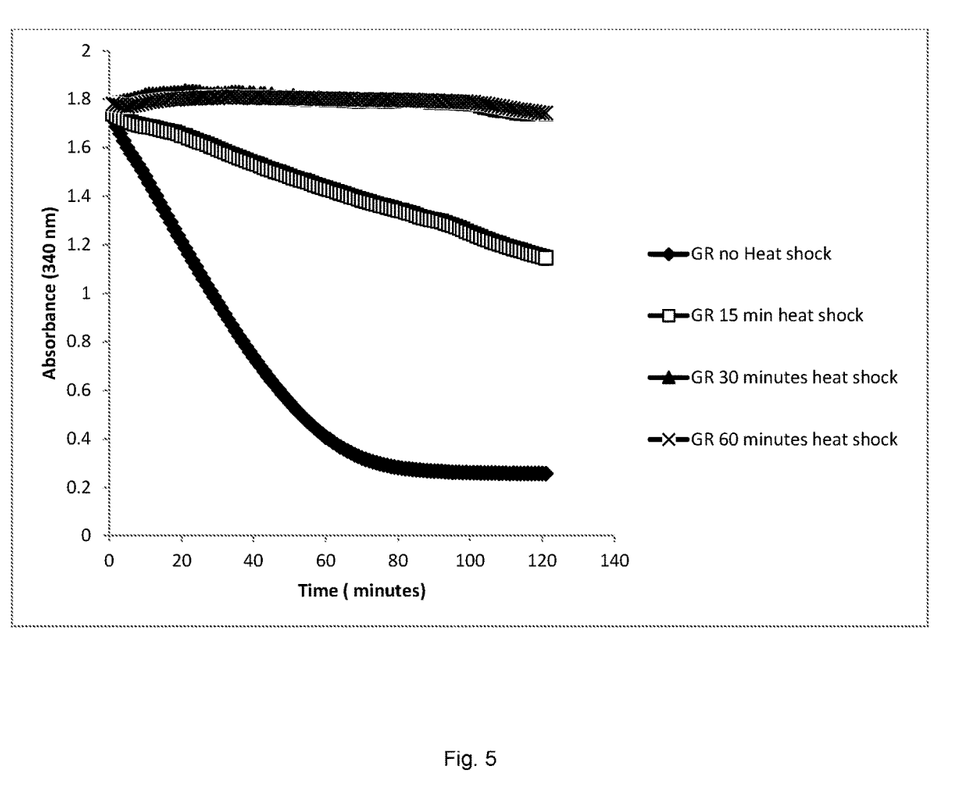
FIG. 5: Glutathione reductase activity before and after incubation at 55° C.

To study the heat stability of glutathione reductase, 1.5 ml of enzyme stock solution was incubated at 55° C. After 15, 30, 60, 120 and 240 minutes of incubation, 250 µl was transferred to a fresh tube and stored in ice-water. The non-incubated stock solutions (~3.5 ml) were directly placed on ice-water, without additional incubation.

The following reaction was performed:

NADPH+GR+GSSG→NADP⁺+GR+2GSH

In the reaction mixture 50 µl Tris-HCL buffer (pH 8.0), 50 µl NADPH, 50 µl glutathione reductase (GR), and 50 µl glutathione oxidized were added. As glutathione reductase, either a non-incubated or heat-treated sample were used. Reactions were carried out in total volume of 200 µl in a flat, clear bottom MTP96 plate. The reactions were carried out at room temperature. All components were mixed except for glutathione. To start the reactions simultaneously, these substrates were added just before placing the MTP96 plate in the µquant spectrophotometer. Absorbance was measured every minute for two hours, at 340 nm.

FIG. 5 shows the results of absorbance in time after incubation at higher temperature. The activity already declines after 15 minutes and no activity is measured after 30 and 60 minutes incubation at 55° C.

Example 8

Yeast Glutathione Reductase Thermostability in Presence and Absence of Protease

20 Units of Yeast Glutathione reductase (Sigma) was added in 10 ml buffer (0.5M Tris HCL buffer) and incubated at 51° C. and pH 5.1 for 18 hours with and without protease in a water bath. Protease applied in this experiment was Alcalase (Novozyme) at the dosage of 0.0068 mg in gram dry mater of the solution. The Enzyme activity was measured after incubation in both solutions using developed assay by spectrophotometer.

TABLE 6

GR activity in the buffer solution before and after incubation with and without Alcalase

| Sample | Before (t = 0) | After (t = 18 h) |
| --- | --- | --- |
| Yeast GR without Alcalase | 2 U/ml | 0.010 U/ml |
| Yeast GR with Alcalase | 2 U/ml | 0.015 |

Results showed that yeast GR enzyme is not thermostable and the activity is lost after incubation at 51 degrees Celsius and pH 5.1 after 18 hours.

Assay for Glutathione Reductase Activity Measurement

The assay for measuring GR activity was based on the following reaction:

GR+GSSG+NADPH→GR+2GSH+NADP+

Where GSSG=L-glutathione oxidized and GSH=L-glutathione reduced.

Materials Applied were:
Glutathione reductase assay solution:
20 mM NADPH (CAS number: 2646-71-1) in mili-Q (mQ)
20 mM GSSG (CAS number: 27025-41-8) in mQ
200 mM Tris-HCl (pH 7.5, obtained in DSM MBK)
For preparing 45 ml stock solution (50 samples): 17 ml mQ, 22.5 ml 200 mM Tris-HCl (pH 7.5), 500 µl 20 mM NADPH, 5 ml 20 mM GSSG were mixed right before the assay.

Method:
The spectrophotometer was calibrated (types: Ultrospec® 2000 in Genetics and Jasco V-630 in ABC lab 1128) to 0.000 with air. the absorbance of assay stock solution was measured without sample. The result of the analysis was taken as negative control. the enzyme solution was Diluted in 100 mM Tris-HCl (pH 7.5). 100 µl of diluted sample was added to 900 µl assay stock solution in a cuvet and was mixed thoroughly with pipette. The cuvet was placed in the spectrophotometer and the absorbance of the solution was recorded at time zero (t=0) and after 1 minute (t=1).

Calculations:

The enzyme activity was determined by the formula below:

$$\text{Activity}[U/ml] = \frac{Df * \Delta A \min^{-1} * Av}{d * e * Sv}$$

Where:
Df=dilution factor
ΔA=absorbance increase/decrease per minute $\min^{-1}$
Av=assay volume in ml (1 ml)
d=optical path length in cm (for cuvet, this is 1 cm)
e=molar extinction coefficient of NADPH, which is 6.22 $M^{-1}$ $cm^{-1}$
Sv=sample volume in ml (0.1 ml)

The invention claimed is:

1. A method for enzymatic reduction of cystine to cysteine comprising contacting cystine with a reduction solution comprising:
    (i) purified active glutathione reductase (EC1.8.1.7);
    (ii) a cofactor; and
    (iii) purified glutathione;
and recovering a cysteine comprising composition, wherein the reduction solution has a pH of at least 6 during contacting with cystine.

2. The method according to claim 1, wherein said recovering the cysteine comprising composition is carried out within 15 hours after contacting cystine with the reduction solution.

3. The method according to claim 1, wherein the cofactor is nicotinamide adenine dinucleotide phosphate (NADPH), optionally in oxidized form (NADP+) or nicotinamide adenine dinucleotide (NADH), optionally in oxidized form (NAD+).

4. The method according to claim 1, wherein the reduction solution further comprises:
    (iv) a cofactor regeneration system comprising glucose dehydrogenase and glucose or formate dehydrogenase and formate.

5. The method according to claim 1, wherein the molar ratio of the glutathione:
cystine in the reduction solution is less than 0.1.

6. The method according to claim 1, wherein the reduction solution has a pH within the range of 7.0 to 8.5.

7. The method according to claim 1, wherein the cystine is contacted with the reduction solution for a time period which is sufficient to reduce more than 50% of the cystine to cysteine.

8. The method according to claim 1, wherein contacting the cystine with the reduction solution is carried out under anaerobic conditions.

9. The method according to claim 1, wherein the cysteine comprising composition comprises cysteine and one or more selected from gluconic acid, formic acid, glucose, formate, nicotinamide adenine dinucleotide phosphate, nicotinamide adenine dinucleotide, glutathione and glutathione reductase.

* * * * *